United States Patent
Lerman et al.

[11] Patent Number: 6,100,400
[45] Date of Patent: Aug. 8, 2000

[54] PROCESS FOR THE PREPARATION OF ESTERS OF [2-[4-[(4-CHLOROPHENYL) PHENYLMETHYL]-1-PIPERAZINYL]-ETHOXY]ACETIC ACID

[75] Inventors: Ori Lerman, Ramat Gan; Erez Gal; Joseph Kaspi, both of Givatayim, all of Israel

[73] Assignee: Chemiagis, Ltd., Israel

[21] Appl. No.: 09/292,318

[22] Filed: Apr. 15, 1999

[30] Foreign Application Priority Data

Apr. 23, 1998 [IL] Israel ......................................... 124195

[51] Int. Cl.[7] .................................................. C07D 295/15
[52] U.S. Cl. ................................................................ 544/396
[58] Field of Search ............................................. 544/396

[56] References Cited

U.S. PATENT DOCUMENTS

| | | | |
|---|---|---|---|
| 4,525,358 | 6/1985 | Baltes et al. ............................. | 514/255 |
| 5,519,016 | 5/1996 | Kimura et al. .......................... | 514/212 |
| 5,550,129 | 8/1996 | Nöldner et al. ......................... | 514/253 |

FOREIGN PATENT DOCUMENTS

| | | |
|---|---|---|
| 2 225 320 | 5/1990 | United Kingdom . |
| 2 225 321 | 5/1990 | United Kingdom . |
| 97/37982 | 10/1997 | WIPO . |

*Primary Examiner*—Emily Bernhardt
*Attorney, Agent, or Firm*—Banner & Witcoff, Ltd.

[57] ABSTRACT

The invention provides a process for the preparation of esters [2-[4-[(4-chlorophenyl)phenylmethyl]-1-piperazinyl] ethoxy]acetic acid, of the formula (I)

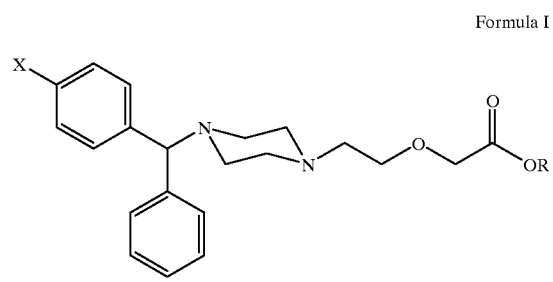

Formula I wherein X represents a halogen atom and R represents a lower alkyl group comprising reacting:

(a) a compound of the formula (II)

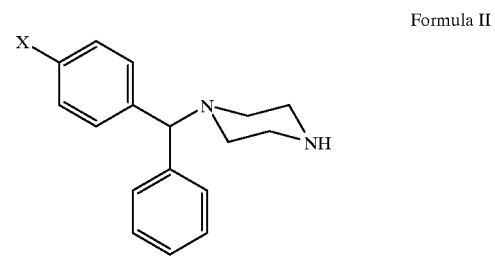

Formula II (b) a compound of the formula (III)

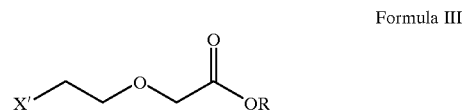

Formula III and (c) a tertiary amine as a solvent and as an acid scavenger at a temperature of at least 100° C., wherein X is a halogen atom, X' is selected from the group consisting of bromine and chlorine and R is a lower alkyl group.

10 Claims, No Drawings

PROCESS FOR THE PREPARATION OF ESTERS OF [2-[4-[(4-CHLOROPHENYL) PHENYLMETHYL]-1-PIPERAZINYL]-ETHOXY]ACETIC ACID

FIELD OF INVENTION

The present invention relates to a process for the preparation of esters of [2-[4-[(4-chlorophenyl)phenylmethyl]-1-piperazinyl]-ethoxy]acetic acid.

STATE OF THE ART

The above-mentioned compounds are essential intermediates in the preparation of cetirizine dihydrochloride, a non sedative antihistaminic drug.

EP 058 146 teaches the use of cetirizine dihydrochloride as a drug, in addition to disclosing synthetic pathways for the preparation thereof. The synthetic pathways for the preparation of cetirizine dihydrochloride (formula IV),

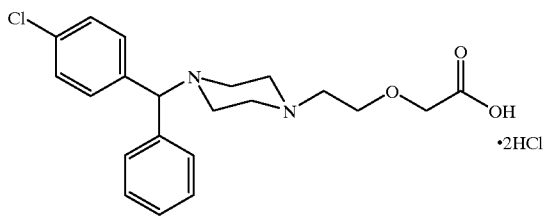

comprises the condensation of 1-[(4-chlorophenyl) phenylmethyl]piperazine (compound 2) with 2-haloethoxyacetic acid derivatives (compound 3), according to the following reaction:

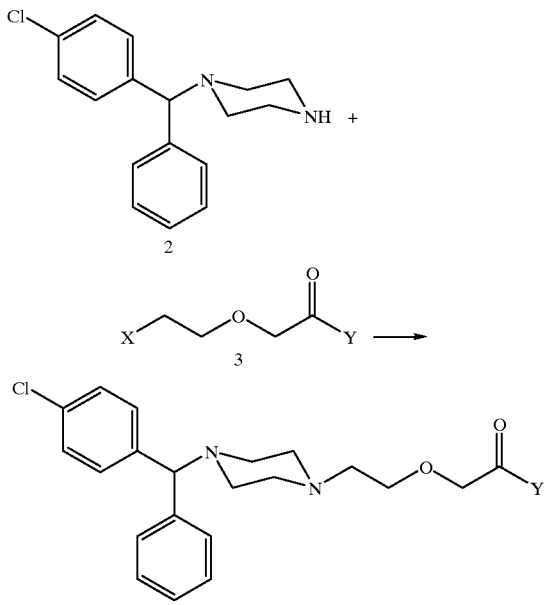

wherein X is chlorine or bromine and Y is alkoxy or amino group.

The condensation, as described in European patent number 058146, is carried out as follows: compounds 2 and 3 are dissolved in xylene and heated in the presence of anhydrous sodium carbonate as an acid scavenger. The yields, as reported therein, are rather low, 54.7% when Y=NH$_2$ and 27.8% when Y=OCH$_3$. Further hydrolysis and pH correction would lead to cetirizine dihydrochloride.

The above-mentioned yields may not satisfy commercial requirements. Thus, there exists a need for a process which will result in greater in yields.

Surprisingly, the present inventors have found a process resulting in significantly higher yields.

SUMMARY OF INVENTION

Thus, there is now provided a process for the preparation of esters [2-[4-[(4-chlorophenyl)phenylmethyl]-1-piperazinyl]ethoxy]acetic acid, of the formula (I)

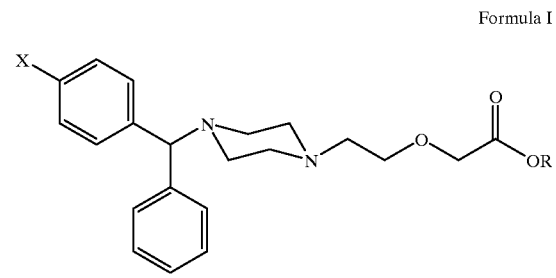

Formula I wherein X represents a halogen atom and R represents a lower alkyl group comprising reacting:

(a) a compound of the formula (II)

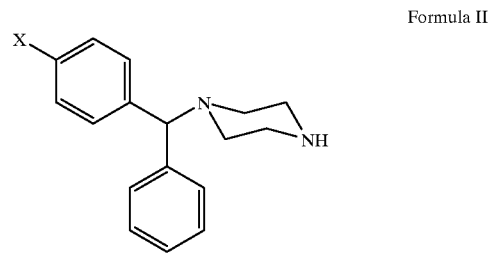

Formula II (b) a compound of the formula (III)

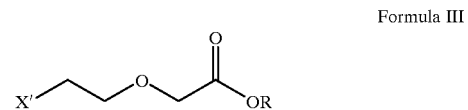

Formula III and (c) a tertiary amine as a solvent and as an acid scavenger at a temperature of at least 100° C., wherein X is a halogen atom, X' is selected from the group consisting of bromine and chlorine and R is a lower alkyl group.

Preferably in the process of the present invention the compound of formula III is present in excess.

In a preferred embodiment of the present invention said tertiary amine is triethylamine.

In a further embodiment of the present invention said process is carried out in the presence of an iodide ion catalyst.

Preferably said catalyst is selected from the group consisting of potassium iodide and tetrabutylammonium iodide.

In a preferred embodiment said reaction is carried out at a temperature of about 130–140° C.

In a further preferred embodiment said reaction is carried out in a pressure vessel.

In an even further preferred embodiment X' is a chlorine atom and R is an ethyl group.

In a most preferred embodiment said reaction is carried out with a molar excess of 1.5–1.6 of the 2-haloethoxyacetic acid ester over1-[4-halophenyl)phenylmethyl]piperazine.

The present inventors have found that when the reaction is performed in a tertiary amine as both solvent and acid scavenger at elevated temperature, significantly higher yield is obtained. Namely, when 1-[(4-chlorophenyl) phenylmethyl]piperazine is reacted in a pressure vessel with ethyl 2-chloroethoxyacetate in triethylamine at 135° C. for 10 hours, ethyl [2-[4-[(4-chlorophenyl)phenylmethyl]-1-piperazinyl]ethoxy]acetate is obtained in 89% yield. When catalytic amounts of potassium iodide or tetrabutylammonium iodide are present in the reaction, slightly higher yield is obtained. If triisopropylamine or pyridine are used instead of triethylamine and the reaction is carried out at the same temperature at atmospheric pressure, a drop of 30–40% in the reaction yield is observed.

It should be noted that similar results were obtained when methyl 2-chloroethoxyacetate was used as a reagent.

This drastic yield improvement caused by the above described variation can lead to an efficient and commercially acceptable synthetic pathway for the preparation of cetirizine dihydrochloride.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLES

Example 1

10 gr. (0.035 mole) of 1-[(4-chlorophenyl)phenylmethyl]piperazine, 8.8 gr. (0.0525 mole) of ethyl 2-chloroethoxyacetate and 50 ml. of triethylamine were introduced into a pressure vessel. The mixture was stirred at 135° C. for 10 hours. It was cooled to 20° C. and filtered. The filtrate was evaporated and then distilled at 10 mbar pressure in order to remove the excess of the unreacted ethyl 2-chloroethoxyacetate. The oily residue obtained is sufficiently pure for the preparation of cetrizine by hydrolysis. The residue was purified over a silica gel chromatographic column. 13 gr. of ethyl [2-[4-[(4-chlorophenyl)phenylmethyl]-1-piperazinyl]ethoxy]acetate is obtained as dark red oil (89.4% yield).

Example 2

10 gr. of (0.035 mole) of 1-[(4-chlorophenyl)phenylmethyl]piperazine, 8.06 gr. (0.0525 mole) of methyl 2-chloroethoxyacetate and 50 ml. of triethylamine were introduced into a pressure vessel and treated in a similar way as described in example 1. 12.5 gr. of methyl [2-[4-[(4-chlorophenyl)phenylmethyl]-1-piperazinyl]ethoxy]acetate is obtained as reddish oil (88.7% yield).

Example 3

10 gr. (0.35 mole) of 1-[(4-chlorophenyl)phenylmethyl]piperazine, 8.6 gr. (0.0525 mole) of ethyl 2-chloroethoxyacetate and 50 ml. of triisopropylamine were stirred and heated to 135° C. for 10 hours and then treated as described in example 1. 7.7 gr. of product has been obtained (53% yield).

Example 4

10 gr. (0.035 mole) of 1-[(4-chlorophenyl)phenylmethyl] piperazine, 8.8 gr. of ethyl 2-chloroethoxyacetate, 0.4. gr. of tetrabutylammonium iodide and 50 ml. of triethylamine were introduced into a pressure vessel and treated as described in example 1. 13.2 gr. of ethyl [2-[4-[(4-chlorophenyl)phenylmethyl]-1-piperazinyl]ethoxy]acetate is obtained (90.8% yield).

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the preparation of esters [2-[4-[(4-halo)phenylmethyl]-1-piperazinyl]ethoxy]acetic acid, of the formula (I)

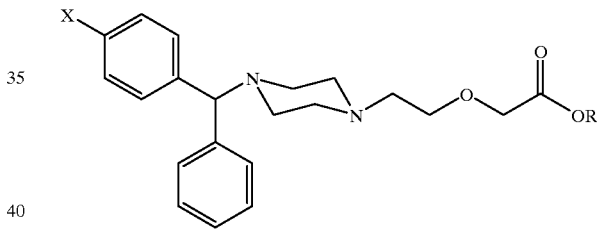

Formula I wherein X represents a halogen atom and R represents a lower alkyl group comprising reacting:

(a) a compound of the formula (II)

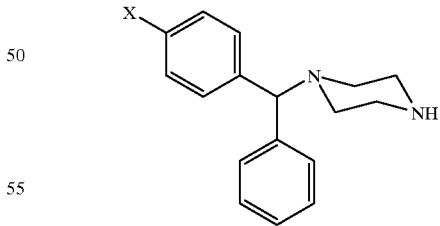

Formula II (b) a compound of the formula (III)

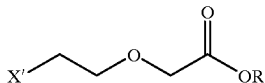

Formula III and (c) a tertiary amine as a solvent and as an acid scavenger at a temperature of at least 100° C., wherein X is a halogen atom, X' is selected from the group consisting of bromine and chlorine and R is a lower alkyl group.

2. A process according to claim 1, wherein the compound of formula III is present in excess.

3. A process according to claim 1, wherein said tertiary amine is triethylamine.

4. A process according to claim 1, wherein said process is carried out in the presence of an iodide ion catalyst.

5. A process according to claim 4, wherein said catalyst is selected from the group consisting of potassium iodide and tetrabutylammonium iodide.

6. A process according to claim 1, wherein said reaction is carried out at a temperature of about 130–140 C.

7. A process according to claim 6, wherein said reaction is carried out in a pressure vessel.

8. A process according to claim 1 wherein X' is chlorine atom.

9. A process according to claim 1 wherein R is an ethyl group.

10. A process according to claim 1 wherein said reaction is carried out with a molar excess of 1.5–1.6 of the 2-haloethoxyacetic acid ester over 1-[4-halophenyl)phenylmethyl]piperazine.

* * * * *

UNITED STATES PATENT AND TRADEMARK OFFICE
CERTIFICATE OF CORRECTION

PATENT NO.: 6,100,400
DATED: August 8, 2000
INVENTOR: Ori LERMAN *et al.*

It is certified that an error appears in the above-identified patent and that said Letters Patent is hereby corrected as shown below:

On the Cover Page, in the Assignee data:

"Chemiagis" has been replaced with --Chemagis--.

In Claim 1, column 4, line 27:

"(4-halo)" has been replaced with --4-halophenyl--.

In Claim 6, column 6, line 2:

"140 C" has been replaced with --140° C--.

Signed and Sealed this

Fifteenth Day of May, 2001

NICHOLAS P. GODICI

*Attest:*

*Attesting Officer*   *Acting Director of the United States Patent and Trademark Office*